(12) United States Patent
Nishie et al.

(10) Patent No.: US 9,422,576 B2
(45) Date of Patent: Aug. 23, 2016

(54) CELL CAPABLE OF PRODUCING ADENO-ASSOCIATED VIRUS VECTOR

(71) Applicant: TAKARA BIO INC., Shiga (JP)

(72) Inventors: Toshikazu Nishie, Shiga (JP); Fuyuko Takashima, Shiga (JP); Tatsuji Enoki, Shiga (JP); Junichi Mineno, Shiga (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 14/409,134

(22) PCT Filed: Jun. 26, 2013

(86) PCT No.: PCT/JP2013/067488
§ 371 (c)(1),
(2) Date: Dec. 18, 2014

(87) PCT Pub. No.: WO2014/007120
PCT Pub. Date: Jan. 9, 2014

(65) Prior Publication Data
US 2015/0291980 A1     Oct. 15, 2015

(30) Foreign Application Priority Data
Jul. 6, 2012  (JP) ................................ 2012-152124

(51) Int. Cl.
| | | |
|---|---|---|
| C12N 5/10 | (2006.01) |
| C12N 15/86 | (2006.01) |
| C12N 15/09 | (2006.01) |
| C12N 15/11 | (2006.01) |
| C12N 7/00 | (2006.01) |
| C12N 15/64 | (2006.01) |
| C12P 19/34 | (2006.01) |

(52) U.S. Cl.
CPC .............. *C12N 15/86* (2013.01); *C12N 5/10* (2013.01); *C12N 7/00* (2013.01); *C12N 15/09* (2013.01); *C12N 15/111* (2013.01); *C12N 15/64* (2013.01); *C12P 19/34* (2013.01); *C12N 2310/141* (2013.01); *C12N 2330/51* (2013.01); *C12N 2750/14143* (2013.01); *C12N 2750/14151* (2013.01)

(58) Field of Classification Search
CPC ............... C12N 5/10; C12N 15/64; C12N 2750/14151
See application file for complete search history.

(56) References Cited

U.S. PATENT DOCUMENTS

| | | | |
|---|---|---|---|
| 5,622,856 A | 4/1997 | Natsoulis |
| 6,093,570 A | 7/2000 | Ferrari et al. |
| 6,475,769 B1 | 11/2002 | Wilson et al. |
| 6,482,633 B1 | 11/2002 | Colosi |
| 6,897,063 B2 | 5/2005 | Colosi |
| 6,995,010 B1 | 2/2006 | Ueno et al. |
| 7,485,458 B2 | 2/2009 | Colosi |
| 2006/0205079 A1 | 9/2006 | Lynch et al. |
| 2008/0171715 A1* | 7/2008 | Brown ................ C12N 15/111 514/44 A |
| 2008/0293141 A1 | 11/2008 | Chono et al. |
| 2011/0130442 A1 | 6/2011 | Kosaka et al. |

FOREIGN PATENT DOCUMENTS

| | | |
|---|---|---|
| CN | 101532024 | 9/2009 |
| CN | 101787373 | 7/2010 |
| CN | 101967496 | 2/2011 |
| CN | 102311973 | 1/2012 |
| WO | 97/06272 | 2/1997 |
| WO | 97/17458 | 5/1997 |
| WO | 01/32899 | 5/2001 |
| WO | 2006/035829 | 4/2006 |
| WO | 2009/148137 | 12/2009 |
| WO | 2010/065630 | 6/2010 |
| WO | WO 2011101869 A1 * | 8/2011 ......... A61K 31/7088 |

OTHER PUBLICATIONS

International Search Report issued Aug. 6, 2013 in International (PCT) Application No. PCT/JP2013/067488.
International Preliminary Report on Patentability issued Jan. 15, 2013 in International (PCT) Application No. PCT/JP2013/067488.
Kambara, H. et al., Establishment of a Novel Permissive Cell Line for the Propagation of Hepatitis C Virus by Expression of MicroRNA miR122, J. Virol., 2011, vol. 86, No. 3, pp. 1382-1393.
Munson et al., A novel miRNA produced during lytic HSV-1 infection is important for efficient replication in tissue culture, Arch. Virol., Jun. 2012, vol. 157, pp. 1677-1688.
Aparicio et al., Adenovirus Virus-Associated RNA is Processed to Functional Interfering RNAs Involved in Virus Production, J. Virol., 2006, vol. 80, No. 3, pp. 1376-1384.
Randall et al., Cellular cofactors affecting hepatitis C virus infection and replication, Proc. Natl. Acad. Sci. USA., 2007, vol. 104, No. 31, pp. 12884-12889.
Hussain et al., West Nile virus encodes a microRNA-like small RNA in the 3' untranslated region which up-regulates GATA4 mRNA and facilitates virus replication in mosquito cells, Nucleic Acids Res., 2011, vol. 40, No. 5, pp. 2210-2223.
Sonntag et al., A viral assembly factor promotes AAV2 capsid formation in the nucleolus, Proc. Natl. Acad. Sci, USA, Jun. 1, 2010, vol. 7, 107, No. 22, pp. 10220-10225.

(Continued)

*Primary Examiner* — J. E. Angell
(74) *Attorney, Agent, or Firm* — Wenderoth, Lind & Ponack, L.L.P.

(57) ABSTRACT

According to the present invention, an AAV vector having a higher titer compared with those of conventional ones can be produced using a cell into which a nucleic acid capable of expressing miRNA is introduced artificially. An AAV vector produced using the cell and a composition containing the viral vector as an active ingredient are very useful as gene transfer means in the studies or clinical practice of gene therapies.

4 Claims, No Drawings

(56) References Cited

OTHER PUBLICATIONS

Chinese Office Action dated Dec. 4, 2015, issued in corresponding Chinese Patent Application No. 201380046350.5. (with English translation).
Extended European Search Report dated Jan. 16, 2016, issued in corresponding European Patent Application No. 13813664.3.
Alexis J. Wallen et at, "Enhancers of Adeno-associated Virus AAV2 Transduction via High Throughput siRNA Screening", The American Society of Gene & Cell Therapy, vol. 19, No. 6, 2011, pp. 1152-1160.
Hui Lu et at, "Systemic Elimination of de novo Capsid Protein Synthesis from Replication-Competent AAV Contamination in the Liver", Human Gene Therapy, vol. 22, No. 5, May 1, 2011, pp. 625-632.
Wenhong Tian et al., "High-Throughput Functional MicroRNAs Profiling by Recombinant AAV-Based MicroRNA Sensor Arrays", PLOS ONE, vol. 7, No. 1, Jan. 5, 2012, p. e29551.

WM Grady et at, "Epigenetic silencing of the intronic microRNA hsa-miR-342 and its host gene EVL in colorectal cancer", Oncogene, vol. 27, Jan. 1, 2008, pp. 3880-3888.
Yong Li et al., "Ratio of miR-196s to HOXC8 Messenger RNA Correlates with Breast Cancer Cell Migration and Metastasis", Cancer Research, vol. 70, No. 20, Aug. 24, 2010, pp. 7894-7904.
M. Papetti et at, "Myb12, downregulated during colon epithelial cell maturation, is suppressed by miR-365", Am J Physiol Gastrointest Liver Physiol, vol. 301, No. 3, Jul. 7, 2011, pp. G508-G518.
A. Nicolas et al., "Identification of Rep-Associated Factors in Herpes Simplex Virus Type 1-Induced Adeno-Associated Virus Type 2 Replication Compartments", Journal of Virology, vol. 84, No. 17, Jun. 23, 2010, pp. 8871-8887.
J. Fraser Wright, "Transient Transfection Methods for Clinical Adeno-Associated Viral Vector Production", Human Gene Therapy, vol. 20, Jul. 1, 2009, pp. 698-706.
Tomaž Bratkovič et al., "Exploiting microRNAs for cell engineering and therapy", Biotechnology Advances, vol. 30, No. 3, Jan. 21, 2012, pp. 753-765.

* cited by examiner

CELL CAPABLE OF PRODUCING ADENO-ASSOCIATED VIRUS VECTOR

TECHNICAL FIELD

The present invention relates to a cell capable of producing an adeno-associated viral vector with a high titer, in particular useful for gene transfer into human, in the study or clinical field of gene therapy.

BACKGROUND ART

At present, many attempts of gene therapy using a viral vector have been made for the purpose of treatment of cancer or infection as well as treatment of congenital genetic disease. As the viral vector, in many cases, a retroviral vector or an adenoviral vector is conventionally used.

An adeno-associated virus (AAV) is a linear single-stranded DNA virus and can infect cells of a broad range of species including human. AAV also infects non-dividing cells in which differentiation terminates, including blood cells, muscle cells, nerve cells and the like. In addition, since AAV is not pathogenic to human, it has a low risk of adverse effect, and the viral particle of AAV is stable. For these reasons, development of AAV vectors for gene transfer is recently proceeding.

For production of an AAV vector for gene transfer, just like other viral vectors, of elements essential for formation of the viral particle which are present on the wild-type AAV genome the elements that need to be provided in cis and the elements that can be provided in trans are separately introduced into a cell for viral production and expressed in the cell, thereby production of wild-type AAV and self-replication of an AAV vector in a host infected with the AAV vector are prevented (Patent Literature 1).

An established conventional process for producing an AAV vector comprises 1) introduction of an AAV vector plasmid in which an ITR placed at each end of the wild-type AAV genome is left and rep and cap genes are removed, 2) introduction of a plasmid for expression of rep and cap genes to provide Rep and Cap proteins in trans, and since AAV needs provision of supplemental elements from a so-called helper virus such as an adenovirus, a herpesvirus, or a vaccinia virus for formation of the infectious viral particle, 3) infection with an adenovirus (Patent Literature 2).

However, the AAV vector obtained by the above-mentioned process is theoretically contaminated with the adenovirus. The adenovirus contamination needs to be removed or inactivated, which is responsible for decrease in AAV vector titer. In addition, there is a worry that administration of the AAV vector contaminated with adenovirus to a human may cause a side effect such as adenovirus infection or inflammation. Thus, a process for producing an AAV vector comprising, instead of the above-mentioned step 3), step 3') introduction of a helper plasmid expressing only elements essential for formation of an AAV viral particle among adenovirus-derived elements (Helper-free system) has been developed (Patent Literature 3. The AAV vector produced according to such a process is not contaminated with an adenovirus, and therefore it is excellently safe.

On the other hand, for production of an AAV vector intended for use in the study or clinical field of gene therapy, it is necessary to obtain a viral vector solution with a high titer. For this purpose, a cell line constantly expressing the rep and cap genes was generated based on a human-derived HeLa cell or A549 cell, and attempts to control the expression levels of these genes were made. However, the AAV vector thus obtained does not have enough titer. Therefore, a process for producing an AAV vector with a higher titer is desired.

CITATION LIST

Patent Literatures

Patent Literature 1: U.S. Pat. No. 6,093,570
Patent Literature 2: WO97/06272
Patent Literature 3: WO97/17458

SUMMARY OF INVENTION

Problems to be Solved by the Invention

An objective of the present invention is to provide a cell for obtaining an AAV vector solution with a high titer without complicated operations, and a process and a kit for producing an AAV vector which comprises use of the cell.

Solutions to the Problems

As mentioned above, for production of an AAV vector intended for use in the study or clinical field of gene therapy, a process enabling production of an AAV vector with a higher titer is desired. The present inventors intently studied, and finally found that an AAV vector with a higher titer than that obtained by conventional methods was obtained by using a cell expressing an artificially introduced miRNA, for example hsa-miR-196a1, hsa-miR-324 or hsa-miR-342, in production of the AAV vector. Thus, the present invention was completed.

The present invention is outlined as follows. The present invention relates to:

[1] A cell capable of producing an AAV vector, wherein an artificially introduced miRNA is expressed,

[2] The cell according to [1], wherein the artificially introduced miRNA is at least one selected from the group consisting of hsa-miR-196a1, hsa-miR-324, and hsa-miR-342,

[3] An AAV vector-producing cell, which is the cell according to [1] or [2] into which a nucleic acid to be enclosed in a virus has been introduced,

[4] A process for producing an AAV vector, the process comprising a step of culturing the cell according to [3],

[5] A kit for production of an AAV vector, comprising a nucleic acid for providing a miRNA and a nucleic acid for providing elements essential for formation of the viral particle of an AVV vector,

[6] An AAV vector obtainable by the process according to [4],

[7] A method for selecting a miRNA that can cause an increase in the ability of an AAV vector-producing cell to produce an AAV vector by expression of the miRNA in the AAV vector-producing cell, the method comprising a step of Preparing a mixture of AAV vectors expressing miRNAs and a step of selecting an AAV vector highly produced in the cell and

[8] The method according to [7] including the following steps (a) to (e):

(a) a step of obtaining a mixture of AAV vectors expressing miRNAs;

(b) a step of infecting a cell with the mixture of AAV vectors expressing miRNAs;

(c) a step of culturing the cell obtained by step (b) to obtain an AAV vector mixture produced from the cell;

(d) a step of repeating steps (b) and (c) one or more times using the AAV vector mixture obtained by step (c); and (e) a step of obtaining a nucleic acid encoding the miRNA in the AAV vector mixture obtained by step (d).

Effects of the Invention

According to the present invention, a cell capable of producing an AAV vector is provided. By using the cell, an AAV vector with a higher titer than that obtained by conventional methods can be produced without complicated operations. In addition, a process and a kit for producing an AAV vector which comprises use of the cell are provided.

MODE FOR CARRYING OUT THE INVENTION

The cell capable of producing an AAV vector of the present invention (hereinafter, referred to as the cell of the present invention) is a cell expressing elements necessary for production of an AAV vector and an artificially introduced miRNA. The AAV vector-producing cell of the present invention is the cell of the present invention into which a nucleic acid to be enclosed in a viral particle has been introduced.

For production of the cell of the present invention, a cell to be used as a material is not particularly limited. Examples of the cell include cells of mammals such as human, monkey, and rodent, and preferable examples thereof include a 293 cell (ATCC CRL-1573), a 293T cell (ATCC CRL-11268), a 293F cell, a 293FT cell (all manufactured by Life Technologies), a G3T-hi cell (WO06/035829), and commercially available cell lines for AAV vector production, for example an AAV293 cell (manufactured by Stratagene Corp.), which have high transformation efficiency and constantly express adenovirus E1 genes. Also, a cell modified to transiently or constantly express some of proteins necessary for AAV vector production can be used.

Examples of the elements necessary for production of an AAV vector include (A) AAV-derived Rep and Cap proteins, and (B) adenovirus-derived elements, for example, E1a, E1b, E2, E4, VA RNA genes. Examples of a nucleic acid for providing the cell of the present invention with elements essential for formation of the viral particle of an AVV vector include (a) a nucleic acid encoding the Rep protein, a nucleic acid encoding the Cap protein, and (b) a nucleic acid encoding adenovirus-derived elements. The forms of these nucleic acids are not limited. These nucleic acids can be inserted into a plasmid or a viral vector as one or more nucleic acid constructs capable of providing the cell used with each element, and then the nucleic acid constructs can be introduced into the cell. For example, a pAAV-RC1 plasmid and a phelper plasmid (manufactured by Cell Biolabs, Inc.) which are commercially available are used. The nucleic acid encoding the Cap protein encodes an assembly-activating protein (AAP) necessary for formation of an AAV particle in an open reading frame different from that of the encoded Cap protein (Proc. Natl. Acad. Sci. USA, 2010, Vol. 107, pp. 10220-10225). Unless otherwise noted, as used herein, the "nucleic acid encoding the Cap protein" means a nucleic acid encoding AAP in addition to the Cap protein. When such a mutation as to destroy the function of AAP (spontaneously or artificially) occurs in the nucleic acid encoding the Cap protein, a nucleic acid encoding AAP may be further introduced into the cell of the present invention. Since nucleic acids encoding E1a and E1b proteins are inserted and constantly expressed in the genome of a 293 cell or the like as mentioned above, it is not necessary to introduce the nucleic acids into the cell. The nucleic acids encoding E1a and E1b proteins may be introduced depending on the cell used, if necessary.

Examples of a method for introduction of the nucleic acid construct include a transient introduction method and a constant introduction method. The transient introduction method is not particularly limited, and a known transient introduction method can be used, including a calcium phosphate method, a lipofection method, a DEAL dextran method, a polyethyleneimine method, and an electroporation method. Also, commercially available reagents, for example TransIT (registered trademark)-293 Reagent, TransIT (registered trademark)-2020 (manufactured by Mirus Bio LLC), Lipofectamine 2000 Reagent (manufactured by Life Technologies), Lipofectamine 2000CD Reagent (manufactured by Life Technologies), FuGene (registered trademark) Transfection Reagent (manufactured by Promega KK.), etc. may be used.

The method of constantly introducing a nucleic acid into a cell is not particularly limited, and a known constant introduction method can be used, including a method comprising use of a retroviral vector, and a method comprising introduction of a nucleic acid into a cell in the same manner as a transient introduction method for a plasmid and selection of the cell in which the nucleic acid is integrated in the chromosome. For the method comprising use of a retroviral vector, commercially available reagents, for example Retrovirus Constructive System (manufactured by Takara Bio Inc.), may be used.

A preferable example of the miRNA in the present invention is a miRNA that can cause an increase in the ability of an AAV vector-producing cell to produce an AAV vector by expression of the miRNA in the AAV vector-producing cell.

The miRNA that can cause an increase in the ability of an AAV vector-producing cell to produce an AAV vector by expression of the miRNA in the AAV vector-producing cell can be easily selected by a person skilled in the art using a selection method as disclosed herein (hereinafter referred to as the selection method of the present invention). The selection method of the present invention comprises steps of preparing a library (mixture) of AAV vectors each of which expresses a different miRNA (for example, human miRNA) in a cell, and then selecting AAV vectors produced at a high level in the cell from the library.

An example of a method of preparing the AAV vector library comprises preparing nucleic acid constructs in which nucleic acids encoding a miRNA library are ligated to a nucleic acid to be enclosed in a viral particle, and then applying a known method to the nucleic acid constructs to obtain AAV vectors carrying the miRNA library. For preparation of the nucleic acid constructs, for example, a pAAV-MCS expression vector (manufactured by Cell Biolabs, Inc.) which is a commercially available AAV vector plasmid can be used. Then, cells suitable for preparation of an AAV vector-producing cell (for example, AAV293 cells) are infected with the AAV vectors carrying the miRNA library. Into the cells, then, a nucleic acid construct encoding elements necessary for production of an AAV vector is transiently introduced. The cells are cultured to obtain a mixture of AAV vectors produced from the cells. Using the AAV vectors thus obtained, a cycle of the above-mentioned steps (infection, culture, and acquisition of vector) is repeated more than one time. By repeating the cycle, AAV vectors carrying nucleic acids for expressing miRNAs that cause an increase of AAV vector production are concentrated in the AAV vector mixture. With regard to the AAV vectors in the AAV vector mixture thus obtained, the nucleotide sequences of miRNAs carried on the AAV vectors are determined. The miRNAs that become obtained more frequently as a result of repeats of the above-mentioned cycle are identified, and they are regarded as miRNAs that cause an increase of AAV vector production. The miRNAs thus selected can be preferably as the miRNA in the cell of the present invention. Examples of the miRNAs include hsa-miR-196a1, hsa-miR-324, and hsa-miR-342.

The nucleotide sequences of RNAs composing the hsa-miR-196a1, hsa-miR-324, and hsa-miR-342 are known, and the DNA sequences encoding them are respectively registered as NCBI GENE ID: 406972, 442898, and 442909. In addition, miRNA expression plasmid vectors carrying the above-mentioned sequences are commercially available from Takara Bio Inc., etc.

The cell of the present invention is prepared by artificial introduction of a nucleic acid for expressing the miRNA as mentioned above. A method for the artificial introduction is not particularly limited. For example, the nucleic acid for expressing the miRNA is transiently or constantly introduced in the form of a nucleic acid construct, for example a plasmid or the like. The carrying form of the nucleic acid construct is not limited. The nucleic acid construct may carry only the nucleic acid for expressing the miRNA, or the nucleic acid for expressing the miRNA may be carried by the same nucleic acid construct that carries a nucleic acid for providing elements necessary for AAV vector production or a nucleic acid to be enclosed in a viral particle.

A nucleic acid to be enclosed in a viral particle is introduced into the cell capable of producing an AAV vector of the present invention to prepare the AAV vector-producing cell of the present invention. The AAV vector-producing cell thus prepared is also one aspect of the present invention. The nucleic acid to be enclosed in a viral particle is composed of ITR sequences derived from AAV and a nucleic acid desired to be carried by an AAV vector. Examples of the nucleic acid desired to be carried by an AAV vector include any foreign gene, for example a nucleic acid encoding a polypeptide (enzyme, growth factor, cytokine, receptor, structural protein, etc.), an antisense RNA, a ribozyme, a decoy, an RNA that induces RNA interference, or the like. For control of expression of the foreign gene, a suitable promoter, enhancer, terminator and other transcriptional regulatory elements may be inserted into the nucleic acid. The nucleic acid to be enclosed in a viral particle can be introduced in the form of a plasmid into a cell. The plasmid can be constructed, for example, by use of a pAAV-MCS expression vector (manufactured by Cell Biolabs, Inc.) which is commercially available, or the like.

Production of the AAV vector of the present invention is performed by culture of an AAV vector-producing cell obtained by a method comprising a step of transiently or constantly introducing the nucleic acid to be enclosed in a viral particle into the cell of the present invention. A method of transiently or constantly introducing the nucleic acid is not particularly limited, and for example, the known transient introduction method or constant introduction method mentioned above as an introduction method of a nucleic acid construct may be used.

Preferably, when the nucleic acid for expressing the miRNA is introduced transiently in the form of an expression plasmid which carries the nucleic acid for expressing the miRNA alone or together with a nucleic acid encoding the Rep protein and/or Cap protein, the present invention exerts more potent effects.

In production of an AAV vector according to the present invention, culture of an AAV vector-producing cell can be performed under known culture conditions. Examples of the culture conditions include, but not limited to, culture at a temperature of 30 to 37° C., a humidity of 95%, and a $CO_2$ concentration of 5 to 10%. The cell culture may be performed at a temperature, a humidity and a $CO_2$ concentration out of the above-mentioned ranges, as long as desired cell growth and production of an AAV vector are attained.

A medium for culture is not particularly limited as long as it allows culture of the AAV vector-producing cell of the present invention and production of an AAV vector is attained. Examples of the medium include known media and serum-free media, for example DMEM, IMDM, Ham's F12, and RPMI-1640, which are commercially available from Lonza, Life Technologies, Sigma-Aldrich Co. LLC, etc. The medium may contain fetal bovine serum (FDS), human serum-derived albumin, etc.

A culture period is not particularly limited. For example, the culture is continued for 12 to 72 hours, preferably 48 to 72 hours. An AAV vector solution can be obtained from a culture supernatant, or a centrifugation supernatant of a cell homogenate obtained by resuspension of collected cells in a suitable buffer solution and then homogenization. In the present invention, the culture supernatant or centrifugation supernatant thus obtained is stored as it is, or by a suitable method (for example, freezing) after it is filtered with a filter or concentrated or purified by a known method to obtain an AAV vector solution, until it is used for the desired purpose.

The AAV vector produced by using the AAV vector-producing cell of the present invention is not particularly limited. Examples of the AAV vector include recombinant AAV vectors derived from existing AAV serotypes or wild-type AAV freshly obtained from nature. A recombinant AAV vector based an an AAV serotype desired to be used can be produced by selecting suitable materials, for example a nucleic acid encoding the Rep protein or a nucleic acid encoding the Cap protein, when the cell of the present invention is produced. For example, also produced is an AAV vector in which a nucleic acid encoding the Rep protein is removed from the nucleic acid to be enclosed in a viral particle in order to prevent insertion of the DNA enclosed in the viral particle into the genome of a target cell and increase an insert region for a foreign gene.

As used herein, the extent of AAV vector production is shown as a titer of the AAV vector. The titer of an AAV vector is a) the genome number (genomic titer) obtained from AAV vector particles which are normally formed or b) the infection ability (infectious titer) of an AAV vector to a cell as determined experimentally, in a certain amount of a sample. The extent of AAV vector production is specified, as necessary.

Examples of a method for determination of the genomic titer include a method comprising treatment of an AAV vector-containing sample with a nuclease and then a protease to degrade nucleic acid impurities in the sample, and then detection of the copy number of the virus genome in the sample by PCR.

Examples of a method for determination of the infectious titer include a method comprising infection of a suitable target cell with a serially diluted solution of an AAV vector-containing sample, detection of expression of a transgene and change in the form of the cell (cytopathy), and determination of the copy number of a provirus introduced into the cell.

According to the present invention, a pharmaceutical composition containing an AAV vector obtained by using the AAV vector-producing cell of the present invention as an effective ingredient is also provided. The pharmaceutical composition can be appropriately prepared according to a technique for production of an AAV vector formulation for gene therapy. For example, the AAV vector obtained by the production method of the present invention can be concentrated and purified by a known method and then formulated into a pharmaceutical composition. The pharmaceutical composition can be used ex vivo for cells from a patient, or administered directly to a patient.

Therefore, the present invention also provides a treatment method comprising administration of a pharmaceutical composition containing an AAV vector obtained by using the AAV vector-producing cell of the present invention as an effective ingredient. Furthermore, the present invention provides use of an AAV vector obtained by using the AAV vector-producing cell of the present invention, in manufacture of a medicament. The present invention also provides an AAV vector obtained using the AAV vector-producing cell of the present invention, for use in treatment.

A kit for production of an AAV vector-producing cell can be prepared by combining a nucleic acid for expressing a miRNA to be used for production of the cell of the present invention, and a nucleic acid for providing elements essential for formation of the viral particle of an AVV vector (a nucleic acid encoding the Rep protein, a nucleic acid encoding the Cap protein, a nucleic acid encoding adenovirus-derived proteins). All of the above-mentioned nucleic acids may be combined or they may be combined appropriately to prepare a nucleic acid construct(s) for providing the desired RNA or protein within a cell. The kit can contain the nucleic acid construct(s). The kit may further contain a vector for preparation of the nucleic acid to be enclosed in a viral particle, or a suitable cell.

EXAMPLES

Hereinafter, the present invention is more specifically explained by way of Examples which the present invention is not limited to.

Example 1

Construction of pAAV-AsRed2-miRNA Library Plasmid

An about 1.6 kb fragment of a pAsRed2-C1 vector (manufactured by Clontech Laboratories, Inc.) ranging from the CMV promoter to the polyA signal was obtained by PCR. At the same time, amplification primers containing a recognition site for NotI were used to add a NotI recognition site to each end of the PCR product. This fragment was treated with NotI (manufactured by Takara Bio Inc.), and then used as an insertion fragment. On the other hand, a pAAV-MCS vector (manufactured by Cell Biolabs, Inc.) was treated with NotI to obtain an about 2.9 kb fragment. This fragment was used as a vector fragment. The vector fragment and the insert fragment were ligated by use of a DNA ligation kit <Mighty Mix> (manufactured by Takara Bio Inc.) to obtain a recombinant plasmid. With the recombinant plasmid, E. coli HST08 premium competent cells (manufactured by Takara Bio Inc., hereinafter referred to as Escherichia coli) were transformed to obtain transformants. Plasmid DNAs were extracted from the transformants, and the plasmid into which a CMV promoter, an AsRed2 coding region, a multiple cloning site (MCS) and a polyA signal were inserted in order from upstream to downstream was selected. This plasmid was referred to as a pAAV-AsRed2 vector.

The pAAV-AsRed2 vector was treated with BglII (manufactured by Takara Bio Inc.) and HindIII (manufactured by Takara Bio Inc.). On the other hand, a human miRNA library cloned into pBApo-CMV DNA (manufactured by Takara Bio Inc.) was treated with BamHI (manufactured by Takara Bio Inc.) and HindIII to obtain fragments of miRNA coding regions. The miRNA coding region fragments were ligated to the pAAV-AsRed2 vectors by use of a DNA ligation kit (manufactured by Takara Bio Inc.), provided that a miRNA containing an internal recognition site for BamHI or HindIII was ligated to the pAAV-AsRed2 vector by directional cloning by use of an In-Fusion (registered trademark) advantage PCR cloning kit (manufactured by Clontech Laboratories, Inc.). Recombinant plasmids thus obtained were used as pAAV-AsRed2-miRNA library plasmids in the following experiments.

Example 2

Production of AAV-miRNA Library Vector (1) Seeding of AAV293 Cell

AAV293 cells (manufactured by Stratagene Corp.) were suspended in DMEM (manufactured by Sigma-Aldrich Co. LLC) containing 10% FBS (manufactured by Thermo Scientific) and mM sodium L-glutamate at $2.5 \times 10^5$ cells/mL. Four milliliters of the suspension was added to a 60 mm dish for cell culture (manufactured by IWAKI), and cultured overnight in an incubator at 5% $CO_2$ and 37° C. (hereinafter, referred to as a $CO_2$ incubator at 37° C.)

(2) Introduction of Plasmid into AAV293 Cell

The pAAV-AsRed2-miRNA library plasmid obtained by Example 1, a pHelper plasmid and a pAAV-RC1 plasmid (both manufactured by Cell Biolabs, Inc.) (each 4 μg) were used to transfect the AAV293 cells of Example 2-(1) by a calcium phosphate method. After 6 hours, the medium was completely removed. Four milliliters of DMEM containing 2% FBS and 2 mM sodium L-glutamate was added, and the cells were cultured in a $CO_2$ incubator at 37° C. for further 48 hours.

(3) Collection of AAV-miRNA Library Vector

The medium was removed from the AAV293 cells cultured by Example 2-(2), and 1 mL of PBS (manufactured by Nacalai Tesque) was added. The AAV293 cells were collected in a 1.5 mL tube by pipetting, and centrifuged at 4° C. and 700×g for 5 minutes. A supernatant was removed. The AAV293 cells were resuspended in 0.1 mL of PBS, and then, subjected 3 times to a series of treatment consisting of freezing in ethanol/dry ice for 2 minutes, thawing in a water bath at 37° C. for 2 minutes, and stirring by a vortex mixer for 1 minute. Then, a cell homogenate containing AAV-miRNA library vectors was collected. The cell homogenate was centrifuged at 4° C. and 10,000×g for 10 minutes. Then, a supernatant was collected as an AAV-miRNA library vector solution.

Example 3

Determination of Genomic Titer of AAV Vector (1) DNase Treatment

To 2 μL of the AAV-miRNA library vector solution, 2 μL of 10×DNaseI buffer, 15.2 μL of water for injection (manufactured by Otsuka Pharmaceutical Co., Ltd.), and 0.8 μL of DNaseI (manufactured by Takara Bio Inc.) were added to prepare a reaction solution. The reaction solution was incubated with TaKaRa PCR Thermal Cycler Dice (registered trademark) Standard (manufactured by Takara Bio Inc.) at 37° C. for 1 hour to degrade free genomes and plasmids. Thereafter, the reaction solution was heated at 99° C. for 10 minutes to inactivate DNaseI, and then stored at 4° C. or −20° C. until Example 3-(2).

(2) Proteinase K Treatment

To 20 µL of the reaction solution obtained by Example 3-(1), 15 µL of water for injection, 4 of 10×Proteinase K buffer [0.1M Tris-HCl (pH 7.8), 0.1M EDTA, 5% SDS], and 1 µL of proteinase K (manufactured by Takara Bio Inc.) were added. The reaction solution was incubated with TaKaRa PCR Thermal Cycler Dice (registered trademark) Standard (manufactured by Takara Bio Inc.) at 55° C. for 1 hour to liberate the genomes of the AAV vectors. Thereafter, the reaction solution was heated at 95° C. for 10 minutes to inactivate proteinase K. The solution thus prepared was stored at 4° C. or −20° C. as an AAV-miRNA library vector genome solution until it was subjected to real-time PCR.

(3) Real-Time PCR

The AAV vector genome solution prepared in Example 3-(2) was diluted 50 times with water for injection. Using 2 of the dilution as a template, primers shown in SEQ ID NO: 1 (Forward primer 1) and SEQ ID NO:2 (Reverse primer 1) of Sequence Listing, and SYBR (registered trademark) Premix ExTaqII (Perfect Real Time) (manufactured by Takara Bio Inc.), real-time PCR was performed. A reaction solution was prepared following the instructions attached to the kit. As a standard, a solution of a linear DNA obtained by treatment of pAAV-AsRed2 with EcoRI was used instead of the AAV vector genome solution. Real-time PCR was performed by use of Thermal Cycler Dice (registered trademark) Real Time System Single (manufactured by Takara Bio Inc.) under conditions recommend for the instrument. Then, the quantity of the AAV vector genome was determined following the instructions attached to the instrument. The genomic titer was expressed as the number of AAV vector genomes per AAV vector-producing cell (viral genome/cell, hereinafter referred to as VG/cell).

Example 4

Screening of AAV-miRNA Library (1) Seeding of AAV293 Cell

AAV293 cells were suspended in DMEM containing 10% FBS and 2 mM sodium L-glutamate at $2.5 \times 10^5$ cells/mL. Four milliliters of the suspension was added to a 60 mm dish for cell culture, and cultured overnight in a $CO_2$ incubator at 37° C.

(2) Infection of AAV293 Cell with AAV-miRNA Library Vector

After the medium was completely removed from the AAV293 cells cultured in Example 4-(1), the AAV-miRNA library vector solution prepared in Example 2 was diluted with DMEM containing 2% FES, and 2 mL of the dilution was added to the cells so that the multiplicity of infection (moi) was about 850 in terms of genomic titer. The cells were cultured in a $CO_2$ incubator at 37° C. for 2 hours. Then, 2 mL of DMEM containing 2% FBS was added, and the cells were cultured overnight in the $CO_2$ incubator at 37° C.

(3) Transfection of pAAV-RC1 Plasmid and pHelper Plasmid into AAV293 Cell

The AAV293 cells cultured in Example 4-(2) were transfected with each 4 µg of a pAAV-RC1 plasmid and a pHelper plasmid by a calcium phosphate method. After 6 hours, the medium was completely removed. Four milliliters of DMEM containing 2% FBS and 2 mM sodium L-glutamate was added, and the cells were cultured in a $CO_2$ incubator at 37° C. for further 48 hours.

(4) Re-Collection of AAV-miRNA Library Vector

The medium was removed from the AAV293 cells cultured in Example 4-(3), and 1 mL, of PBS was added. The AAV293 cells were collected in a 1.5 mL tube by pipetting, and centrifuged at 4° C. and 700×g for 5 minutes. A supernatant was removed. The AAV293 cells were resuspended in 0.1 mL of PBS, and then, subjected 3 times to a series of treatment consisting of freezing in ethanol/dry ice for 2 minutes, thawing in a water bath at 37° C. for 2 minutes, and stirring by a vortex mixer for 1 minute. Then, a cell homogenate containing AAV-miRNA library vectors was collected. The cell homogenate was centrifuged at 4° C. and 10,000×g for 10 minutes. Then, a supernatant was collected as an AAV-miRNA library vector solution.

(5) Concentration of AAV-miRNA Library Vector

The steps of Example 4-(1) to (4) were repeated a total of 8 times to concentrate the AAV-miRNA library vectors. In each round, the amount of virus at the time of infection (moi) and the amount of virus at the time of collection are shown in Table 1 in terms of genomic titer.

TABLE 1

|  | Virus amount at infection (VG/cell) | Virus amount at collection (VG/cell) | Ratio |
| --- | --- | --- | --- |
| Round 1 | 849 | 716 | 84% |
| Round 2 | 251 | 80 | 32% |
| Round 3 | 56 | 96 | 172% |
| Round 4 | 68 | 23 | 34% |
| Round 5 | 17 | 491 | 2,816% |
| Round 6 | 20 | 147 | 735% |
| Round 7 | 20 | 130 | 650% |
| Round 8 | 20 | 147 | 735% |

As seen from the above table, in round 5 or later, the AAV-miRNA virus easily replicated. Thus, it was found that miRNAs causing an increase of AAV vector production were concentrated.

Example 5

Selection of miRNA Causing an Increase of AAV Vector Production (1) Preparation of AAV-miRNA Vector Genome Using 2 µL of the AAV-miRNA library vector solution collected in each round of Example 4, an AAV-miRNA library vector genome solution was obtained in the same manner as Example 3-(1) and (2).

(2) Cloning of miRNA

A region around the miRNA coding region was amplified by PCR using the AAV-miRNA library vector genome solution obtained by Example 5-(1) as a template, primers shown in SEQ ID NO: 3 (Forward primer 2) and SEQ ID NO:4 (Reverse primer 2) of Sequence Listing, and PrimeSTAR (registered trademark) GXL DNA polymerase (manufactured by Takara Bio Inc.). The reaction was performed by repeating 30 cycles of 98° C. for 10 seconds, 55° C. for 15 seconds and 68° C. for 30 seconds, and then repeating the same conditions one more time. The fragment thus obtained was ligated to pUC118 (manufactured by Takara Bio Inc.) which had been treated with HincII (manufactured by Takara Bio Inc.) and BAP (manufactured by Takara Bio Inc.) by use of the In-Fusion (registered trademark) Advantage PCR cloning kit.

(3) Determination of miRNA Nucleotide Sequence

*Escherichia coli* was transformed with the recombinant plasmid obtained by Example 5-(2), seeded on an LB plate containing ampicillin and then cultured overnight at 37° C. to obtain many colonies. Some of the colonies were selected, and each colony was cultured overnight in an LB liquid medium containing ampicillin. Then, plasmids were extracted from the colonies by use of a Miniprep DNA purification kit (manufactured by Takara Bio Inc.). The plasmids thus obtained were sequenced, and the names of miRNAs encoded on the plasmids were identified. Results are shown in Table 2.

TABLE 2

| Name | Round 4 | Round 5 | Round 6 | Round 7 | Round 8 | Total number of identification |
|---|---|---|---|---|---|---|
| hsa-miR-324 | 9 | 7 | 13 | 19 | 24 | 72 |
| hsa-miR-196a1 | 1 | 2 | 3 | 4 | 1 | 11 |
| hsa-miR-342 | | | | 5 | 3 | |
| hsa-miR-125a | | 2 | | 2 | | 4 |
| hsa-miR-145 | | 1 | | 1 | | 2 |
| hsa-miR-518e | | | 2 | | | 2 |
| hsa-miR-645 | | 1 | | | 1 | 2 |
| miRNA001 | | | 2 | | | 2 |
| hsa-miR-106b | | 1 | | | | 1 |
| hsa-miR-124 | 1 | | | | | 1 |
| hsa-miR-125b | | 1 | | | | 1 |
| hsa-miR-205 | 1 | | | | | 1 |
| hsa-miR-30a | 1 | | | | | 1 |
| hsa-miR-30e | | 1 | | | | 1 |
| hsa-miR-335 | | 1 | | | | 1 |
| hsa-miR-483 | | | | 1 | | 1 |
| hsa-miR-494 | 1 | | | | | 1 |
| hsa-miR-499 | | | | | 1 | 1 |
| hsa-miR-513a | 1 | | | | | 1 |
| hsa-miR-515 | | | | 1 | | 1 |
| hsa-miR-516b | | | | 1 | | 1 |
| hsa-miR-517h | | | | 1 | | 1 |
| hsa-miR-550 | | | 1 | | | 1 |
| hsa-miR-633 | | | 1 | | | 1 |
| miRNA101 | | | | 1 | | 1 |
| Number of determined nucleotide sequences | 15 | 15 | 24 | 34 | 32 | 120 |

As shown in the above table, hsa-miR-196a1, 324, 342, etc. were identified multiple times. Therefore, it was found that miRNAs causing an increase of AAV vector production were obtained by repeats of the experimental round.

Example 6

Evaluation of Obtained miRNA (1) Preparation of miRNA Expression Plasmid

From the human miRNA library cloned into pBApo-CMV DNA, the plasmids into which hsa-miR-196a1, hsa-miR-324 and hsa-miR-342 had been inserted were selected. *Escherichia coli* was transformed with each of the plasmid to prepare a large quantity of the plasmids. For the preparation of the plasmids, Nucleobond Xtra Midi EF (manufactured Macherey-Nagel GmbH & Co., KG) was used. The plasmids thus obtained were referred to as pBapo-miR196a1, pBapo-miR324, and pBapo-miR342, respectively.

(2) Production of AAV Vector

AAV293 cells were transfected with the plasmids obtained in Example 6-(1) together with the pAAV-AsRed2-C1 vector, the pAAV-RC1 plasmid, and the pHelper plasmid. As a control, pBApo-CMV was transfected instead of the plasmids obtained in Example 6-(1). Every operation from transfection to collection of AAV vectors was performed in the same manner as Example 2-(1) to (3).

(3) Determination of Genomic Titer of AAV Vector

The genomic titers of the AAV vectors thus obtained were determined in the same manner as Example 3. Results are shown in Table 3.

TABLE 3

| plasmid | Amount of obtained virus (VG/cell) |
|---|---|
| pBApo-CMV DNA | 4,480 |
| pBApo-miR196a1 | 5,464 |
| pBApo-miR324 | 13,261 |
| pBApo-miR342 | 4,606 |

As shown in the above table, when pBApo-miR324, pBApo-miR196a1 or pBApo-miR342 was used, an AAV vector was obtained with a high genomic titer as compared with the control. Particularly, when pBApo-miR324 was used, the AAV vector was obtained with a genomic titer several times higher than that of the control.

Example 7

Evaluation of pRC-miR342 Plasmid (1) Preparation of pRC-miR342 Plasmid

Using pBApo-miR342 as a template and primers shown in SEQ ID NO: 5 (Forward primer 3) and SEQ ID NO:6 (Reverse primer 3) of Sequence Listing, a region ranging from the CMV promoter to the miR342 coding region was amplified by PCP. The fragment thus obtained was ligated to a pAAV-RC1 plasmid which had been treated with SnaBI (manufactured by Takara Bio Inc.) by use of the In-Fusion (registered trademark) Advantage PCP cloning kit. The nucleotide sequence of the recombinant plasmid thus obtained was determined to confirm insertion of the CMV-miR342 fragment. Then, the plasmid was prepared. The plasmid thus obtained was referred to as pRC-miR342.

(2) Evaluation of pRC-miR342

AAV293 cells were transfected with the pRC-miR342 obtained in Example 7-(1) together with the pAAV-AsRed2 vector and the pHelper plasmid. As a control, the pAAV-RC1 plasmid was transfected instead of pRC-miR342. AAV vector-producing cells thus obtained were referred to as 293-RC-miR342 cells and 293-RC cells. Every operation from transfection to collection of AAV vectors was performed in the same manner as Example 2-(1) to (3).

(3) Determination of Genomic Titer of AAV Vector

The genomic titer of an AAV vector obtained from each AAV vector-producing cell obtained by Example 7-(2) was determined in the same manner as Example 3. Results are shown in Table 4.

TABLE 4

| Name of AAV vector-producing cell | Amount of obtained virus (VG/cell) | Average (VG/cell) | ratio |
|---|---|---|---|
| 293-RC cell | 1.31E+04 | 1.29E+04 | 1.64 |
|  | 1.26E+04 |  |  |
| 293-RC-miR342 cell | 1.92E+04 | 2.11E+04 |  |
|  | 2.30E+04 |  |  |

As shown in the above table, the AAV vector-producing cell prepared by use of pRC-miR342 produced an AAV vector with a genomic titer 60% higher than that of the control.

Example 8

Evaluation of Obtained AAV Vector (1) Seeding of Target Cell

AAV293 cells were suspended in DMEM containing 10% FBS and 2 mM sodium L-glutamate at $4 \times 10^4$ cells/mL. One milliliter of the suspension was added to a 24-well plate for cell culture (manufactured by Corning Incorporated), and cultured overnight in a $CO_2$ incubator at 37° C.

(2) Infection with Virus

After the medium was removed from the AAV293 cells cultured in Example 8-(1), 500 µL of DMEM containing 10% FES and 2 mM sodium L-glutamate and then 1 µL of the AAV vector solution obtained by Example 7-(2) were added to the cells. After the cells were cultured in a $CO_2$ incubator at 37° C. for 6 hours, the medium was removed, and 500 µL of DMEM containing 10% FBS and 2 mM sodium L-glutamate was added, followed by culture overnight.

(3) Analysis with Flow Cytometer and Calculation of Infectious Titer

The medium was removed from the AAV293 cells cultured in Example 8-(2), and 500 µL of PBS was added. After treatment with trypsin, 500 µL of a medium wad added and the AAV293 cells were collected in a 1.5 mL tube by pipetting. A cell suspension thus obtained was subjected to a flow cytometer (Cytomics FC500, manufactured by Beckman Coulter, Inc.) to measure a rate of AsRed2 positive cells. Based on the obtained value, an infectious titer was calculated and expressed as the number of infectious AAV vectors in 1 mL of the AAV vector solution (Infectious viral particle/mL, hereinafter referred to as ivp/mL). Results are shown in Table 5.

TABLE 5

| Name of AAV vector-producing cell | Infectious titer of virus (ivp/mL) |
|---|---|
| 293-RC cell | 2.5.E+06 |
| 293-RC-miR342 cell | 3.6.E+06 |

As shown in the above table, the AAV vector produced by use of pRC-miR342 had not only a high genomic titer, but also a high infectious titer. Thus, it was found that introduction of pRC-miR342 into an AAV vector-producing cell caused an increase in the ability of the cell to produce an AAV vector having the normal infection ability.

Example 9

Valuation of pRC6-miR342 and pRC9-miR342 Plasmids (1) Preparation of pRC-miRNA Plasmid After pAAV-RC1 was treated with SmiI and SnaBI and the corresponding site of an AAV type 9 Cap gene was artificially synthesized, they were ligated to construct pRC9. The fragment ranging from the CMV promoter to the miR342 coding region which was amplified in Example 7-(1) was ligated to the pRC9 which was treated with SnaBI in the same manner as Example 7-(1) to obtain pRC9-miR342. In other words, the pRC9-miR342 is a helper plasmid containing the Cap gene of AAV type 9 and the CMV-miR342 fragment. Separately, using pBApo-miR342 as a template and primers shown in SEQ ID NO: 7 (Forward primer 4) and SEQ ID NO:8 (Reverse primer 4) of Sequence Listing, a region ranging from the CMV promoter to the miR342 coding region was amplified by PCR. The fragment thus obtained was ligated to a pRep-Cap AAV6 plasmid (manufactured by Applied Viromics, LLC) which had been treated with SmaI (manufactured by Takara Bio Inc.) by use of the In-Fusion (registered trademark) Advantage PCR cloning kit to obtain pRC6-miR342. In other words, the pRC6-miR342 is a helper plasmid containing the Cap gene of AAV type 6 and the CMV-miR342 fragment.

(2) Evaluation of pRC-miRNA

AAV293 cells were transfected with the plasmids obtained in Example 9-(1) or a control plasmid together with the pAAV-AsRed2 and the pHelper plasmid. Every operation from transfection to collection of AAV vectors was performed in the same manner as Example 2-(1) to (3).

(3) Determination of Genomic Titer of AAV Vector

The genomic titer of the produced AAV vector was determined in the same manner as Example 3. Results are shown in Table 6.

TABLE 6

| plasmid | Amount of obtained virus (VG/cell) |
|---|---|
| pRC6 | 8.4.E+0.2 |
| pRC6-miR342 | 3.9.E+03 |
| pRC9 | 3.6.E+04 |
| pRC9-miR342 | 4.0.E+04 |

As shown in Table 6, when pRC into which miR342 was inserted was used, regardless of whether the pRC was derived from AAV type 6 or AAV type 9, an AAV vector was obtained with a high genomic titer as compared with the control.

INDUSTRIAL APPLICABILITY

By use of the cell of the present invention, AAV vectors can be produced with higher titers as compared with conventional methods. The AAV vector produced by use of the cell of the present invention and a composition comprising the AAV vector as an effective ingredient are very useful as a method for gene introduction in the study or clinical field of gene therapy.

SEQUENCE LISTING FREE TEXT

SEQ ID NO:1: Forward primer 1
SEQ ID NO:2: Reverse primer 1

SEQ ID NO:3: Forward primer 2
SEQ ID NO:4: Reverse primer 2
SEQ ID NO:5: Forward primer 3

SEQ ID NO:6: Reverse primer 3
SEQ ID NO:7: Forward primer 4
SEQ ID NO:8: Reverse primer 4

The invention claimed is:

1. An AAV vector-producing cell wherein the cell comprises and expresses at least one exogenous miRNA selected from the group consisting of hsa-miR-324, hsa-miR-196a1 and hsa-miR-342, and wherein the cell further comprises nucleic acid that expresses the elements essential for formation of the viral particle of an AAV vector, wherein the cell produces the AAV vector.

2. An AAV vector-producing cell, which is the cell according to claim 1 into which a nucleic acid to be enclosed in a virus has been introduced.

3. A process for producing an AAV vector, the process comprising a step of culturing the cell according to claim 2.

4. A kit comprising a nucleic acid that expresses at least one miRNA selected from the group consisting of hsa-miR-324, hsa-miR-196a1 and hsa-miR-342 in combination with a nucleic acid that expresses the elements essential for formation of the viral particle of an AVV vector.

* * * * *

```
                              SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic forward primer 1

<400> SEQUENCE: 1
atcatatgcc aagtacgccc                                                      20

<210> SEQ ID NO 2
<211> LENGTH: 19
<212> TYPE: DNA
<213> ORGANISM: Artificial Sequence
<220> FEATURE:
<223> OTHER INFORMATION: Synthetic reverse primer 1

<400> SEQUENCE: 2
ccaaaaccgc atcaccatg                                                       19

<210> SEQ ID NO 3
<211> LENGTH: 35
<212> TYPE: DNA
<213> ORGANISM: Artificial Sequence
<220> FEATURE:
<223> OTHER INFORMATION: Synthetic forward primer 2

<400> SEQUENCE: 3
ggatcctcta gagtcagctg ggccacaact gagga                                     35

<210> SEQ ID NO 4
<211> LENGTH: 35
<212> TYPE: DNA
<213> ORGANISM: Artificial Sequence
<220> FEATURE:
<223> OTHER INFORMATION: Synthetic reverse primer 2

<400> SEQUENCE: 4
gcatgcctgc aggtccggta ccgtcgactg cagaa                                     35

<210> SEQ ID NO 5
<211> LENGTH: 35
<212> TYPE: DNA
<213> ORGANISM: Artificial Sequence
<220> FEATURE:
<223> OTHER INFORMATION: Synthetic forward primer 3

<400> SEQUENCE: 5
agtttccatg gctactaaat ggcccgcctg gctga                                     35

<210> SEQ ID NO 6
<211> LENGTH: 35
<212> TYPE: DNA
<213> ORGANISM: Artificial Sequence
<220> FEATURE:
<223> OTHER INFORMATION: Synthetic reverse primer 3

<400> SEQUENCE: 6
atgctactta tctacaacga cccaacaccg tgcgt                                     35
```

```
<210> SEQ ID NO 7
<211> LENGTH: 35
<212> TYPE: DNA
<213> ORGANISM: Artificial Sequence
<220> FEATURE:
<223> OTHER INFORMATION: Synthetic forward primer 4

<400> SEQUENCE: 7
cattaactac agccctaaat ggcccgcctg gctga                              35

<210> SEQ ID NO 8
<211> LENGTH: 35
<212> TYPE: DNA
<213> ORGANISM: Artificial Sequence
<220> FEATURE:
<223> OTHER INFORMATION: Synthetic reverse primer 4

<400> SEQUENCE: 8
gctgtttaaa cgcccaacga cccaacaccg tgcgt                              35
```